United States Patent [19]

Leibman

[11] Patent Number: 4,961,234
[45] Date of Patent: Oct. 9, 1990

[54] OUTERGARMENT WITH DETACHABLE CROTCH PIECE

[76] Inventor: Faith H. Leibman, 304 Melrose Rd., Merion, Pa. 19066

[21] Appl. No.: 328,288

[22] Filed: Mar. 24, 1989

[51] Int. Cl.$^5$ .............................................. A41D 1/06
[52] U.S. Cl. .......................................... 2/234; 2/408
[58] Field of Search ...................... 2/227, 234, 80, 114, 2/405, 408, 78 B

[56] References Cited

U.S. PATENT DOCUMENTS

| | | | |
|---|---|---|---|
| 602,188 | 4/1898 | Sittig | 2/408 |
| 1,083,712 | 1/1914 | Uyeda | 2/408 |
| 1,512,171 | 7/1922 | Homling | 2/78 B |
| 2,008,773 | 7/1935 | Shapiro | 2/80 |
| 2,389,273 | 11/1945 | Novak | 2/227 |
| 2,477,593 | 8/1949 | Gershenow | 2/408 X |
| 2,506,324 | 5/1950 | Zywiecka | 2/408 X |
| 2,522,008 | 9/1950 | Wohlman | 2/408 X |
| 3,208,454 | 9/1965 | Farkas | 2/408 X |
| 3,425,063 | 2/1969 | Brown | 2/234 |

FOREIGN PATENT DOCUMENTS

| | | | |
|---|---|---|---|
| 220819 | 9/1957 | Australia | 2/408 |
| 208956 | 10/1907 | Fed. Rep. of Germany | 2/408 |
| 153913 | 7/1938 | Fed. Rep. of Germany | 2/408 |
| 636684 | 5/1950 | United Kingdom | 2/408 |

Primary Examiner—Werner H. Schroeder
Assistant Examiner—Gloria Hale
Attorney, Agent, or Firm—Stuart E. Beck

[57] ABSTRACT

An outergarment having a detachable crotch piece is disclosed. The crotch piece is multilayered, with a disposable liner and a washable backing. The crotch piece is preferably padded for comfort and has a seamless cover layer. In this way, the need for supplementary or separate undergarments is eliminated, while sanitary conditions are maintained.

17 Claims, 2 Drawing Sheets

OUTERGARMENT WITH DETACHABLE CROTCH PIECE

This invention relates to an outergarment and particularly to pants having a detachable, multi-layer crotch piece.

BACKGROUND OF THE INVENTION

When hiking, backpacking or camping, the volume and weight of gear is an important consideration. On an extended trip, it is often not possible to carry sufficient pairs of pants and undergarments, in an attempt to economize on space and weight. Thus, the camper or hiker has no choice other than to frequently wash out these garments, oftentimes under inconvenient circumstances, such as insufficient hot water. Moreover, these garments require a long time to dry, which presents a particular difficulty when the campsite is moved daily.

A further difficulty with use of separate, conventional undergarments is that the undergarments are often visible through the wearer's outergarments. Typically, seam lines show. One current approach to this problem is to utilize undergarments that only cover the crotch area and do not cover any other portion of the abdomen or buttocks. However, these have the distinct disadvantage of causing chafing, particularly when worn during athletic activity.

SUMMARY OF THE INVENTION

The present invention overcomes the above disadvantages by providing an outergarment with a removable crotch piece. The crotch piece is preferably of multilayer construction having a disposable liner layer and a washable outer layer. In this way a hiker or camper need wash only the washable crotch piece, without washing the entire pair of pants, thus significantly reducing drying time. Alternatively, the washable crotch piece may be replaced with a clean crotch piece, while the first is packed away until the camper returns home. Further, sanitary conditions can be maintained merely be replacing the disposable liners and/or washing the outer layer. Additionally the need for supplementary or separate undergarments is eliminated.

In addition, the crotch piece of the outergarment of the present invention eliminates unsightly seam lines. It is also preferably padded for comfort. The outer layer is preferably formed of a two-piece backing layer with a curved seam designed to follow the contour of the person's body and a cover layer made of a seamless construction to eliminate chaffing. The crotch piece also extends partially into the leg opening for additional comfort. This construction also makes it more convenient for women to urinate without taking the entire pair of pants off.

The present invention also permits the changing of a detachable crotch panel for the purpose of maintaining sanitary conditions, particularly in view of the fact that the onset of menses is unpredictable for many women. Thus, a stained crotch piece can easily be removed and replaced immediately with a fresh panel, preferably a fresh panel having fasteners for fastening and correctly positioning a sanitary napkin.

BRIEF DESCRIPTION OF THE DRAWINGS

The above aspects of the present invention can be seen from the attached drawings, in which.

DETAILED DESCRIPTION OF THE PREFERRED EMBODIMENTS

Figure 1:
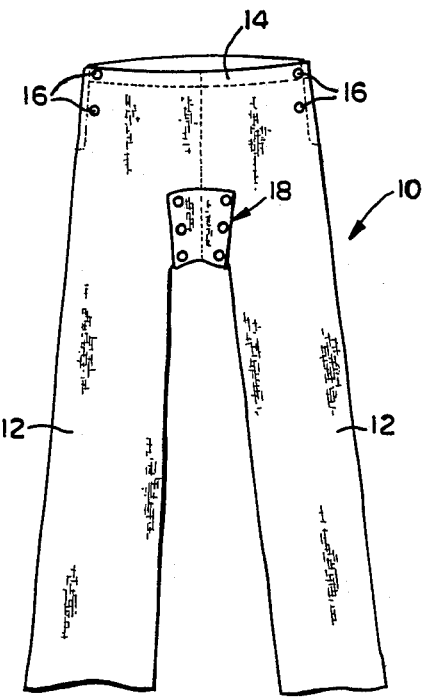
FIG. 1 is a front view of an outergarment with removable crotch piece of the present invention.
Figure 2:
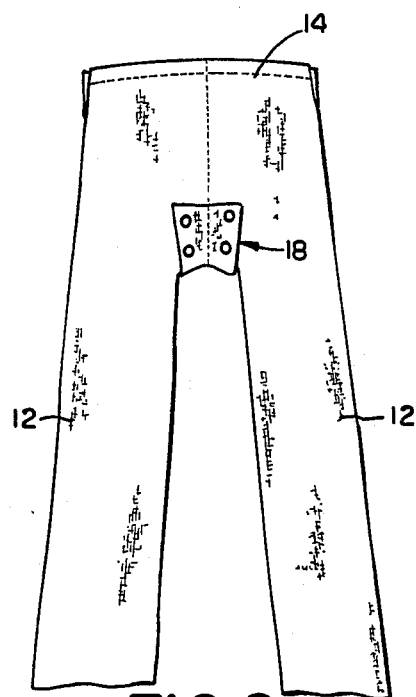
FIG. 2 is a back view of the outergarment of FIG. 1.
Figure 3:
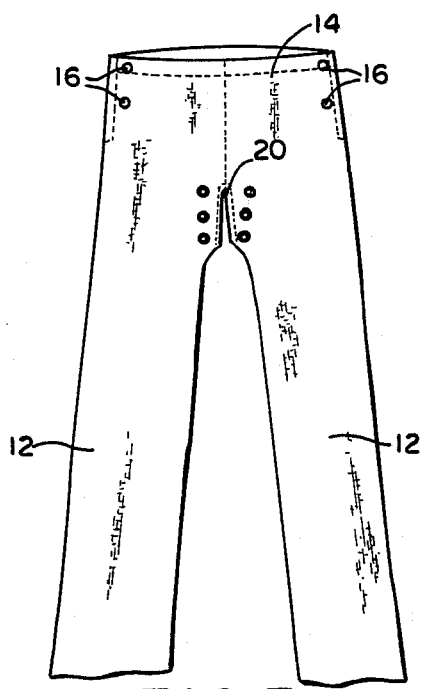
FIG. 3 is a front view of the outergarment of FIG. 1 without the crotch piece attached.
Figure 4:
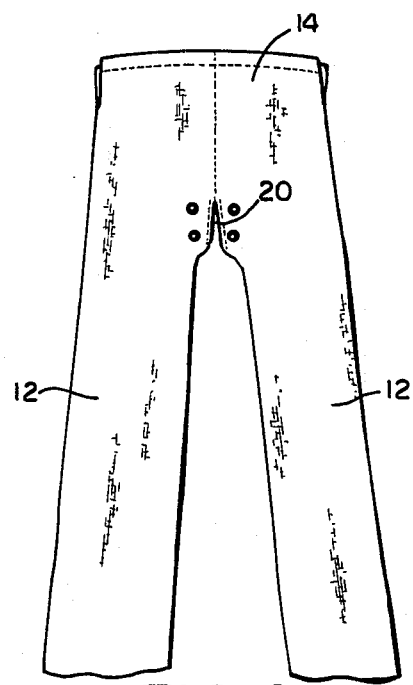
FIG. 4 is a back view of the outergarment of FIG. 3.
Figure 5:
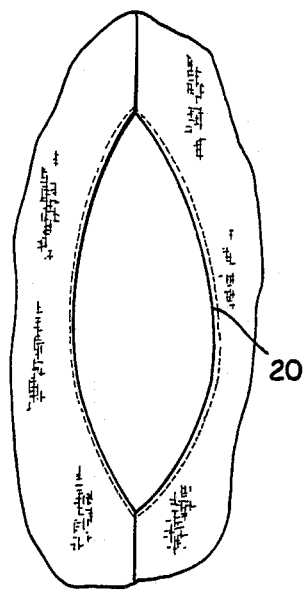
FIG. 5 is a partial view of the outergarment of FIG. 3 showing the crotch opening.

An outergarment with detachable crotch piece according to the present invention is shown in FIGS. 1 and 2 and generally designated 10. Throughout the figures, like elements will be represented by like numerals.

Outergarment 10 includes leg receiving portions 12 and waistband 14. Suitable fasteners 16, such as the snaps shown, are provided for opening and closing the waistband. A crotch piece 18, as described in more detail below, is attached to crotch opening 20. Crotch piece 18 may be removably attached to the leg receiving portions via any suitable means, such as snaps 32.

Figure 6:
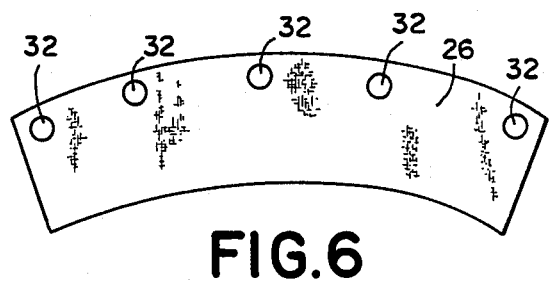
FIG. 6 is a perspective view of one panel of the backing layer of the crotch piece in FIG. 1.
Figure 7:
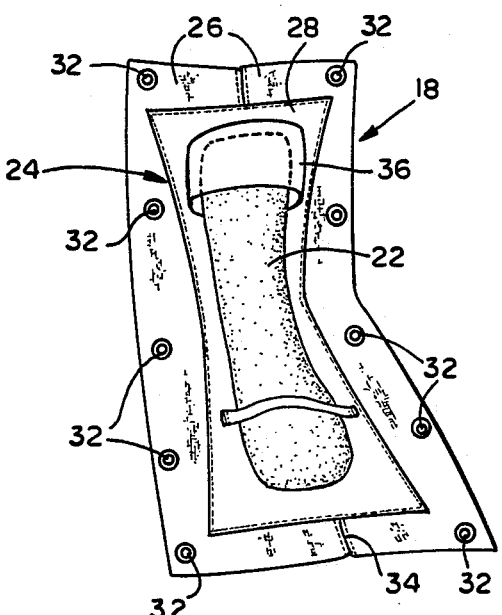
FIG. 7 is a perspective view of the crotch piece of the outergarment of FIG. 1.

Detachable crotch piece 18, as shown in greater detail in FIGS. 6 and 7, includes a inner layer 22 and an outer layer 24. Outer layer 24 is preferably washable, while inner layer 22 is preferably made of a disposable material that will absorb secretions. Alternatively, inner layer 22 may be formed of a typical sanitary napkin.

Inner layer 22 may be removably fastened to outer layer 24 in any suitable manner, such as via loops 30 or via pockets 36 (it is understood that each end may be fastened by loops 30 or pockets 36 or a combination thereof). Thus, the inner layer can be changed to maintain sanitary conditions. Alternatively, the outer layer can be washed and worn alone.

In one preferred embodiment, outer layer 24 is formed of a two-piece backing layer 26 and a seamless cover layer 28. The pieces comprising the backing layer 26 are curved as seen in FIG. 6. They are joined along their inner curved edges by a curved seam 34. Since the pieces are joined in this manner the backing layer will follow the contour of the legs and crotch area and avoid "bunching-up" between the wearer's legs. Cover layer 28 substantially covers seam 34 to prevent chaffing.

This description is for illustrative purposes only. Modifications may be made, particularly with regard to size, shape and arrangement of parts, within the scope of the invention as defined by the appended claims.

what is claimed is:

1. An outergarment for hiking or camping that eliminates the need for a separate undergarmet comprising:

a waistband;

leg receiving portions coupled to said waistband and having leg openings therein;

a detachable crotch piece being made of a washable material and being completely removable from said outergarment, said crotch piece including an outer layer which comprises two curved pieces, said pieces being connected to each other along their inner curved edges by a seam so that said outer layer follows the contour of the crotch; and means for releasably connecting said crotch piece to said outergarment, said releasable connecting means being disposed adjacent to the outer curved edges to said curved pieces and to said leg portions of said outergarment.

2. An outergarment as in claim 1, wherein said crotch piece is padded.

3. An outergarment as in claim 1, wherein said outer washable layer includes a backing layer and a seamless cover layer.

4. An outergarment as in claim 1 wherein said crotch piece extends partially into said leg openings.

5. An outergarment as in claim 1, wherein said releasable connecting means are snaps.

6. An outergarment as in claim 1, wherein said crotch piece further includes an inner disposable layer, loop fastening means connected to said inner layer for attaching said inner disposable layer to said outer washable layer.

7. An outergarment as in claim 6, wherein said crotch piece further includes pocket fastening means for attaching said inner disposable layer to said outer washable layer.

8. A detachable crotch piece for an outergarment which is worn for hiking or camping and which includes leg portions; said crotch piece eliminating the need for a separate undergarment and comprising an outer washable layer which comprises two curved pieces, said pieces being connected to each other along their inner curved edges by a seam so that said outer layer follows the contour of the crotch; and means for releasably connecting said crotch piece to the outergarment, said releasable connecting means being disposed adjacent to the outer curved edges of said curved pieces for connection to the leg portions of said outergarment.

9. A detachable crotch piece as in claim 8, wherein said crotch piece is padded.

10. A detachable crotch piece as in claim 8, wherein said outer washable layer includes a backing layer and a seamless cover layer.

11. A detachable crotch piece as in claim 8, wherein said releasable connecting means are snaps.

12. A detachable crotch piece as in claim 8, wherein said crotch further includes an inner disposable layer, and loop fastening means connected to said inner disposable layer for attaching said inner disposable layer to said outer washable layer.

13. A detachable crotch piece as in claim 8, wherein said crotch piece further includes an inner disposable layer, and pocket fastening means for attaching said inner disposable layer to said outer washable layer.

* * * * *